(12) United States Patent
Akura et al.

(10) Patent No.: US 10,105,129 B2
(45) Date of Patent: Oct. 23, 2018

(54) DRAINING DEVICE AND METHOD OF DRAINING LIQUID IN EYELID APERTURE

(71) Applicant: KUNIMUNE CO., LTD., Osaka (JP)

(72) Inventors: Junsuke Akura, Wakayama (JP); Kiran Pokharel, Hyogo (JP)

(73) Assignee: KUNIMUNE CO., LTD, Osaka (JP)

( * ) Notice: Subject to any disclaimer, the term of this patent is extended or adjusted under 35 U.S.C. 154(b) by 901 days.

(21) Appl. No.: 14/562,057

(22) Filed: Dec. 5, 2014

(65) Prior Publication Data

US 2015/0100044 A1    Apr. 9, 2015

Related U.S. Application Data

(63) Continuation of application No. PCT/JP2013/068810, filed on Jul. 10, 2013.

(30) Foreign Application Priority Data

Jul. 11, 2012  (JP) .................................. 2012-155218

(51) Int. Cl.
*A61M 5/00* (2006.01)
*A61B 17/02* (2006.01)
(Continued)

(52) U.S. Cl.
CPC .......... *A61B 17/0231* (2013.01); *A61M 27/00* (2013.01); *A61F 9/00736* (2013.01);
(Continued)

(58) Field of Classification Search
CPC ....... A61C 3/10; A61B 17/0231; A61B 17/30; A61M 27/00; B25B 9/02; A61F 9/007
See application file for complete search history.

(56) References Cited

U.S. PATENT DOCUMENTS 5,174,279 A * 12/1992 Cobo .................. A61B 17/0231
600/206
6,346,078 B1 * 2/2002 Ellman ............... A61B 17/0231
600/214
(Continued)

FOREIGN PATENT DOCUMENTS

EP    2 198 816 A1    6/2010
JP    08-317939 A    12/1996
(Continued)

OTHER PUBLICATIONS

International Search Report dated Aug. 13, 2013 issued in corresponding PCT/JP2013/068810 application (pp. 1-2).
(Continued)

*Primary Examiner* — Ariana Zimbouski
(74) *Attorney, Agent, or Firm* — Millen, White, Zelano & Branigan, P.C.; William Nixon

(57) ABSTRACT

The draining device 1 is provided with a main body 11 including two side wall members 111 each having a tip end section 111B curved downward, and a connecting portion 12 connecting the side wall members 111. In a manner such that at least upper portions of adjacent side wall members 111 are spaced at a certain distance d and side surfaces 111*a* of the adjacent side wall members 111 face each other, by connecting the side wall members 111 of the main body 11 with the connecting portion 12, a liquid draining passage R for draining a liquid to a space between adjacent side wall members 111. For this reason, since the liquid inflow cross-sectional area S1 and the passage cross-sectional area S2 increase, it becomes possible to introduce a large amount of liquid into the gap between the side wall members and pass therethrough.

14 Claims, 10 Drawing Sheets

(51) Int. Cl.
*A61M 27/00* (2006.01)
*A61F 9/007* (2006.01)
(52) U.S. Cl.
CPC ............ *A61M 2027/004* (2013.01); *A61M 2210/0606* (2013.01); *A61M 2210/0612* (2013.01)

(56) References Cited

U.S. PATENT DOCUMENTS

| | | | |
|---|---|---|---|
| 8,181,654 B2* | 5/2012 | Kanno | A61F 6/04 128/842 |
| 8,517,936 B1* | 8/2013 | Townsend | A61B 17/0231 600/236 |
| 2003/0171656 A1* | 9/2003 | Foulkes | A61B 1/00094 600/232 |
| 2007/0179346 A1 | 8/2007 | Foulkes | |
| 2014/0052110 A1 | 2/2014 | Shiba | |

FOREIGN PATENT DOCUMENTS

| | | |
|---|---|---|
| JP | 2000-060895 A | 2/2000 |
| JP | 4572378 B2 | 11/2010 |
| JP | 4806731 B1 | 11/2011 |

OTHER PUBLICATIONS

English Abstract and Machine Translation for JP4572378, Publication Date: Nov. 4, 2010.
English Abstract and Machine Translation for JP4806731, Publication Date: Nov. 2, 2011.
English Abstract and Machine Translation for JP2000-060895, Publication Date: Feb. 29, 2000.
English Abstract and Machine Translation for JP08-317939, Publication Date: Dec. 3, 1996.

* cited by examiner

DRAINING DEVICE AND METHOD OF DRAINING LIQUID IN EYELID APERTURE

CROSS-REFERENCE TO RELATED APPLICATIONS

This is a continuation of International Application PCT/JP2013/068810, with an international filing date of Jul. 10, 2013, claiming a priority to Japanese Patent Application No. 2012-155218, filed on Jul. 11, 2012, the contents of which are incorporated herein by reference in their entirety.

BACKGROUND OF THE INVENTION

Field of the Invention

The present disclosure relates to a draining device for draining a liquid, which will be accumulated in an eyelid aperture to disturb a surgery, an operation, a medical treatment or the like (hereinafter simply referred to as "surgery or the like"), out of the eyelid aperture during an eye surgery for cataract, etc. The present disclosure also relates to a method of draining a liquid in an eyelid aperture.

Description of the Related Art

The following description of related art sets forth the inventors' knowledge of related art and certain problems therein and should not be construed as an admission of knowledge in the prior art.

In general, during cataract surgery or another eye surgery, in order to maintain transparency of a cornea, a liquid is supplied onto a surface of an eyeball from a syringe or a large amount of liquid is supplied to an eyelid aperture from a surgical machine. If a liquid supplied to an eyelid aperture accumulates in the eyelid aperture, there is a risk to cause deteriorated visibility of the operator due to the accumulated liquid, intraoperative complication, or postoperative bacterial endophthalmitis if bacteria is mixed in the accumulated liquid. Especially, in the case of a person having hollowed-out eyes, there is a tendency to cause liquid stagnation as mentioned above.

As a method for preventing the aforementioned liquid stagnation or accumulation in the eyelid aperture, a method for draining the liquid by soaking up with a gauze or a sponge has been employed. However, this method is very poor in draining ability, and therefore cannot cope with modern surgeries such as ultrasonic cataract surgery in which a large amount of liquid is supplied.

The currently most popular method as a liquid draining method is as follows. According to the method, a hole or a groove is formed in a cavity arm portion of an eyelid retractor for opening an eyelid during surgery. The hole of the arm portion and an electric pump are connected with a tube, so that the liquid accumulated in the eyelid aperture is sucked up via the tube by a suction force of the pump. However, even with this method, in cases where an eye has a thick eyelid or a narrow eyelid, or an eye is hollowed-out which readily causes liquid accumulation or stagnation, sufficient draining ability could not be exerted. Further, there are such disadvantages that it requires a driving power to operate the pump, it emits a large sound at the time of sucking up the liquid, or elderly people's slacked conjunctiva is readily incarcerated in the suction hole of the pump to prevent sucking liquid or produce pain.

In order to cope with the aforementioned problems, as disclosed in, for example, Japanese Patent Publication No. 4572378 (hereinafter referred to as "Patent Document 1") or Japanese Patent Publication No. 4806731 (hereinafter referred to as "Patent Document 2"), draining devices are known. Each of the draining devices is capable of draining a liquid accumulated or stagnated in an eyelid aperture by simply being arranged at an outer canthus (an outer corner of an eye) or an eyelid margin near the outer canthus without using a pump. In such draining devices, a liquid moves through a space formed between a main body of the draining device and an eyelid by a capillary action, etc., to be drained.

Concretely, the draining device disclosed in Patent Document 1 is provided with a main body to be arranged so as to form a predetermined gap between the main body and an arrangement surface of the main body on an eyelid near the outer corner of an eye. This main body has a flat sheet-like structure formed into approximately a trapezoidal shape as a whole in a developed state, and is formed by a waterproof material. Further, the main body is provided with a protruded section which will inwardly protrudes from the eyelid aperture marginal part when used, and the protruded section is provided with a hang-down section which will hang down toward conjunctiva near the outer corner of an eye when used. This causes adhesion of the liquid in the eyelid aperture to the rear surface of the protruded portion to pull out the liquid in the gap between the main body and the arranging surface, and make the liquid pass through the gap between the main body and the arranging surface to be drained outside the main body.

Further, the draining device disclosed in Patent Document 2 has a hook-shaped structure in which the tip end portion of the main body (body portion) is formed into a paddle shape. The draining device is arranged by inserting the hook portion into the eyelid conjunctival sac or drape of the outer corner of an eye. A liquid is caused to pass through the gap between the eyelid margin side surface of the abdominal section of the main body and the eyelid margin or the drape to drain the liquid by guiding to the surface of the tale portion of the main body to be drained.

However, conventional draining devices had a problem that a liquid accumulated or stagnated in an eyelid aperture could not be sufficiently drained outside the eyelid aperture. One of the reasons for this problem resides in that it is difficult to make a liquid effectively flow into the gap between the main body and the eyelid.

In the draining device 91 disclosed in Patent Document 1, as shown in FIG. 15($a$), the main body 911 is arranged or placed on an eyelid M so that the protruded portions 912 protruded from the main body 911 into the inner side of the eyelid margin N absorbs the liquid accumulated or stagnated in the eyelid aperture from the upper side to flow therein. However, in order to absorb the liquid accumulated in the eyelid aperture from the upper side, it is required to set the height of the protruded portion 912 to the position near the conjunctiva L or the eyelid M. For this reason, the height of an inflow port for introducing a liquid is limited, reducing the cross-sectional area (hereinafter referred to as "inflow cross-sectional area") $S11$ of the liquid at the position for introducing the liquid, which cannot effectively introduce the liquid. Further, in absorbing the liquid, only the liquid near the lower surface of the main body 911 can be absorbed, which prevents absorption of a large amount of liquid.

Further, in the draining device 92 disclosed in Patent Document 2, as shown in FIG. 15($b$), the liquid is caused to flow in along the hook portion 922 hooked on the outer corner of an eye (eyelid margin) N. However, there is a limitation in the amount of liquid capable of flowing along the hook portion 922 by capillary action, and therefore the inflow cross-sectional area $S21$ of the liquid is very small. As a result, this draining device 92 also cannot cause effective inflow of the liquid. Further, in this draining device 92, when the liquid in the eyelid aperture increases, the draining device 92 itself dams the liquid at the outer corner of an eye N.

Further, the second reason that a liquid cannot be sufficiently drained resides in the fact that a conventional draining device cannot allow the liquid to efficiently pass through the gap between the main body and the eyelid in draining the liquid.

The draining device 91 of Patent Document 1 is designed to make the liquid pass through the gap between the lower surface of the main body 911 and the eyelid M to drain the liquid. However, as shown in FIG. 15(a), since the liquid is made to pass through the gap for allowing passing of a liquid in a manner in which the gap is closed from the upper side thereof, the gap for allowing passing of the liquid is limited. In accordance with this, the cross-sectional area (hereinafter referred to as "passage area") S12 of the liquid at the position of making the liquid to pass reduces, preventing effective passing of the liquid.

Further, the draining device 92 of Patent Document 2 makes the liquid flow between the lower surface of the main body 921 and the eyelid M or the vicinity thereof. Therefore, as shown in FIG. 15(b), the passage area S22 for the liquid is very small, and the draining device 92 itself prevents passing of the liquid, preventing effective passing of the liquid.

In fact, in both the draining devices of Patent Documents 1 and 2, because of the aforementioned reasons, liquid could not be sufficiently drained outside the eyelid aperture, resulting in stagnation of the liquid in the eyelid because of the liquid supply amount exceeding the discharge amount by the draining device. Further, the draining device of Patent Document 1 is large in width, and the draining device of Patent Document 2 is large in height. This often hinders operations of surgical instruments by a surgical operator performing an operation while sitting at the ear side of a patient.

The description herein of advantages and disadvantages of various features, embodiments, methods, and apparatus disclosed in other publications is in no way intended to limit the present invention. For example, certain features of the described embodiments of the invention may be capable of overcoming certain disadvantages and/or providing certain advantages, such as, e.g., disadvantages and/or advantages discussed herein, while retaining some or all of the features, embodiments, methods, and apparatus disclosed therein.

SUMMARY OF THE DISCLOSURE

The disclosed embodiments of the present disclosure have been developed in view of the above-mentioned and/or other problems in the related art. The disclosed embodiments of the present disclosure can improve upon existing methods and/or apparatuses.

The embodiments of the present disclosure were made to solve the aforementioned problems, and aim to provide a draining device capable of effectively draining a liquid accumulated or stagnated in an eyelid aperture outside the eyelid aperture.

In order to attain the aforementioned objects, some embodiments of the present disclosure provide a draining device for draining a liquid accumulated in an eyelid aperture to an outside of the eyelid aperture during an eye surgery. The draining device includes a main body having a plurality of side wall members, each of the plurality of side wall members having a tip section curved downward, and a connecting portion connecting the side wall members of the main body. In a manner such that at least upper portions of adjacent side wall members are spaced at a certain distance and side surfaces of the adjacent side members face each other, by connecting the side wall members of the main body with the connecting portion, a liquid draining passage for draining a liquid to a space between adjacent side wall members is formed.

According to this embodiment, the liquid draining passage for draining a liquid to the gap formed between the adjacent side wall members is formed and the liquid inflow cross-sectional area of the liquid draining passage increases. As a result, a large amount of liquid can be flowed into the gap between the side wall members. Further, since the liquid passage cross-sectional area of the liquid draining passage increases, a large amount of liquid can be flowed into the gap between the side wall members. As explained above, both the inflow cross-sectional area and the passage area of the liquid draining passage can be increased, enabling a large amount of the liquid to flow in and pass through the liquid draining passage. This in turn makes it possible to effectively drain the liquid accumulated or stagnated in the eyelid aperture outside the eyelid aperture.

Further, it is preferable that the main body is formed so that a tip section of each of the plurality of side wall members is curved into a hook shape. With this, when the tip section is hooked on the eyelid margin, the draining device can be placed or arranged stably.

Further, it is preferable that the main body is provided with a gripping ledge extended from a tip section of the side wall member so as to grip an eyelid margin between the main body and the gripping ledge. With this, by pinching the eyelid margin by and between the main body and the gripping ledge, the draining device can be placed or arranged quickly and stably.

Further, it is preferable that the main body is provided with eyelid opening arms each extending from a tip section of the side wall member along an eyelid margin when used, and each of the eyelid opening arms is equipped with a contact piece which comes into contact with an inner surface of an eyelid margin when used. With this, it becomes possible to drain the liquid in the eyelid opening while opening the upper and lower eyelids with the eyelid opening arms each extending from the tip section.

Further, it is preferable that the inner side surface of the side wall member of the main body is subjected to a honing process or a hairline process. With this, by forming a fine/minute uneven/irregular (concave-convex) shape on a surface of each side wall member by a honing process or forming fine/minute linear scratches, flaws, scars, cuts, scrapes or the like (hereinafter simply referred to as "fine linear scratches") on a surface of each side wall member by a hairline process, the wettability (hydrophilic property) between the inner side surface of the side wall member and the liquid can be enhanced, which enables smooth introduction and passing of a liquid.

Further, the main body can be made of a water absorbing material. With this, apart from the liquid draining passage in which a liquid is flowed in between side wall members and passes therethrough to be drained, another liquid draining passage in which a liquid is absorbed from the tip sections of the side wall members and passes therethrough to be drained is formed. Therefore, the liquid can be drained more effectively.

Further, it is preferable that the main body is formed so that tip sections of the plurality of side wall members are curved in a separating direction. With this, the inflow port for introducing a liquid can be increased, and therefore a more large amount of liquid can be introduced.

Further, it is preferable that the main body is provided with an insertion hole at a rear end section of each of the plurality of side wall members, and an a wire type eyelid retractor is attached to the side wall members with a wire portion of the eyelid retractor inserted in the insertion holes. With this, utilizing a commonly-used wire type eyelid retractor, a liquid can be drained while opening the eyelid margins.

Further, it is preferable that the connecting portion is provided at lower end portions of the side wall members and is provided with an adhesive material on a lower surface of the connecting portion. With this, the connecting portion can be adhered to the eyelid by the adhesive material, and therefore the draining device can be placed or arranged stably.

According to another aspect of the present disclosure, a method of draining a liquid in an eyelid aperture includes preparing the draining device as recited in any one of the aforementioned items, and placing the draining device on an eyelid margin or vicinity thereof with the tip sections of the side wall members arranged in an eyelid aperture.

Further, it is preferable that the connecting portion connects rear end portions of the side wall members in a manner as to urge the tip sections of the side wall members in a separating direction. With this, by fixing the tip sections to the eyelid margins with the urging force, the draining device can be placed or arranged stably.

Further, it is preferable that the connecting portion is provided with a fixing auxiliary member extending in a length direction of the side wall member between the side wall members and having a hook-shaped tip section. With this, by hooking the tip section of the fixing auxiliary member on the eyelid margin, the draining device can be placed or arranged stably.

According to some embodiments of the present disclosure, the liquid draining passage for draining a liquid to a gap formed between adjacent side wall members is formed and the liquid inflow cross-sectional area of the liquid draining passage increases. As a result, a large amount of liquid can be made to flow into the gap between the side wall members. Further, since the liquid passage cross-sectional area of the liquid draining passage increases, a large amount of liquid can be made to flow into the gap between the side wall members.

As explained above, in some embodiments of this disclosure, both the inflow cross-sectional area and the passage area of the liquid draining passage can be increased, enabling a large amount of the liquid to flow in and pass through the liquid draining passage. This makes it possible to effectively drain the liquid accumulated or stagnated in the eyelid aperture outside the eyelid aperture.

Further, when the draining device is placed or arranged in a manner as to bridge the eyelid margins, it becomes possible to always maintain the liquid draining effects with less influence due to the difference among individuals in the thickness or shape of an individual eyelid.

Further, by constituting the draining device so as to have a liquid draining efficiency equal to or similar to the liquid draining efficiency of a conventional draining device, by, e.g., decreasing the size of the side plate member and/or decreasing the distance between the side plate members, the space occupied by the present draining device can be reduced.

Further, when placing or arranging the draining device, any troublesome operations, such as, e.g., bending something or the like, will not be required, which enables quick initiation of a surgery or the like.

Further, the draining device itself will not dam a liquid at the eyelid margin, and it becomes possible to assuredly cope with regardless of the supplied amount of liquid into the eyelid aperture.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/ or advantages of particular embodiments should not be construed as limiting other embodiments or the claims. In the drawings, the size and relative sizes of layers and regions may be exaggerated for clarity. Like numbers refer to like elements throughout. The terminology used herein is for the purpose of describing particular embodiments only and is not intended to be limiting of the disclosure. As used herein, the singular forms "a", "an" and "the" are intended to include the plural forms as well, unless the context clearly indicates otherwise. As used herein, the term "and/or" includes any and all combinations of one or more of the associated listed items and may be abbreviated as "/". It will be understood that, although the terms first, second, etc. may be used herein to describe various elements, these elements should not be limited by these terms. Unless indicated otherwise, these terms are only used to distinguish one element from another. For example, a first object could be termed a second object, and, similarly, a second object could be termed a first object without departing from the teachings of the disclosure. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. It will be understood that when an element is referred to as being "connected" or "coupled" to or "on" another element, it can be directly connected or coupled to or on the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.). However, the term "contact," as used herein refers to direct contact (i.e., touching) unless the context indicates otherwise. Terms such as "same," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to reflect this meaning. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

BRIEF DESCRIPTION OF THE DRAWINGS

The disclosed embodiments of the present disclosure are shown by way of example, and not limitation, in the accompanying figures.

DETAILED DESCRIPTION

In the following paragraphs, some embodiments of the disclosure will be described by way of example and not limitation. It should be understood based on this disclosure that various other modifications can be made by those in the art based on these illustrated embodiments.

<First Embodiment>

Next, a first embodiment of a draining device according to the present disclosure will be explained with reference to FIGS. 1 to 4.

[Structure of Draining Device 1]

Figure 1:
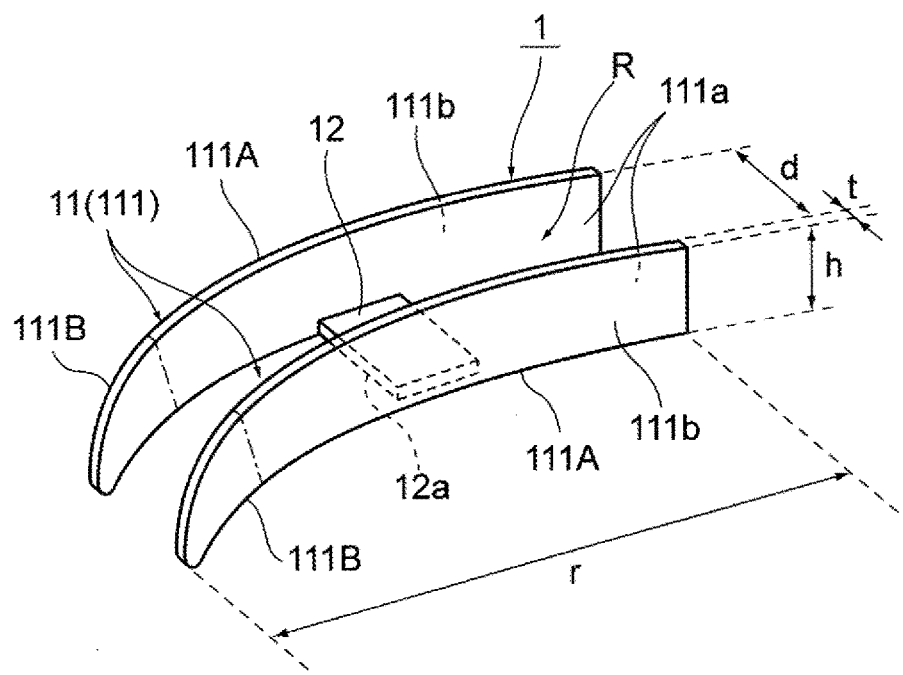
FIG. 1 is a perspective view illustrating a draining device according to a first embodiment of the present disclosure.

The draining device 1 according to this embodiment is, as shown in FIG. 1, provided with a main body 11 including two side wall members 111 and 111 and a connecting portion 12 connecting the side wall members 111 and 111 of the main body 11.

The main body 11 is constituted by two plate-shaped side wall members 111 and 111, and the side wall members 111 and 111 are formed into the same shape with the same material. Concretely, each side wall member 111 is an elongated plate-shaped member having a length r, a height h, and a thickness t, and has an inner side surface 111a positioned on the inner side and an outer side surface 111b positioned on the outer side. Each side wall member 111 includes a rectangular base section 111A extending from a rear end portion to the front side, and a tapered tip section 111B slightly curbed downward from the forward end portion of the base section 111A. In FIG. 1, the boundary portion of the base section 111A and the tip section 111B is shown by a dashed line which is a virtual line illustrated for the purpose of explanation.

Further, this side wall member 111 is made of a hard material, such as, e.g., stainless steel, and the inner side surface 111a of each side wall member 111 is subjected to a hairline process. The hairline process is a process for forming fine linear scratches extending from the forward side of the inner side surface 111a of each side wall member 111 toward the rearward side thereof. This enhances the wettability (or hydrophilic property) between a liquid and the inner side surface 111a of each side wall member 111 in the direction for making a liquid flow in and pass through, which makes it possible to smoothly introduce a liquid from the tip section 111B and pass the liquid toward the rear end portion of the base section 111A.

The connecting portion 12, as shown in FIG. 1, connects the side wall members 111 of the main body 11 in a side-by-side manner. Concretely, the connecting portion 12 is a plate-shaped member with a width d. One end portion of the connecting portion 12 in the width direction is connected to the lower center of the inner side surface 111a of one of the side wall members 111 in an orthogonally-crossed manner. In the same manner, the other end portion of the connecting portion 12 is connected to the lower center of the inner side surface 111a of the other side wall member 111 in an orthogonally-crossed manner. Therefore, the side wall members 111 and 111 are arranged at a predetermined distance d and the inner side surfaces 111a and 111a face each other in parallel, so that a liquid draining passage R for draining a liquid is formed between the adjacent side wall members 111 and 111.

Figure 3:
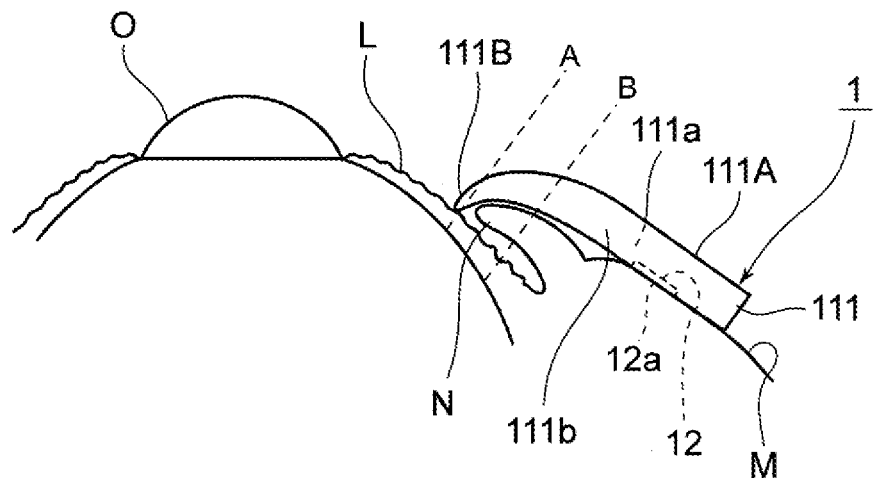
FIG. 3 is a side view illustrating the set status of the draining device according to the first embodiment of the present disclosure.
Figure 4:
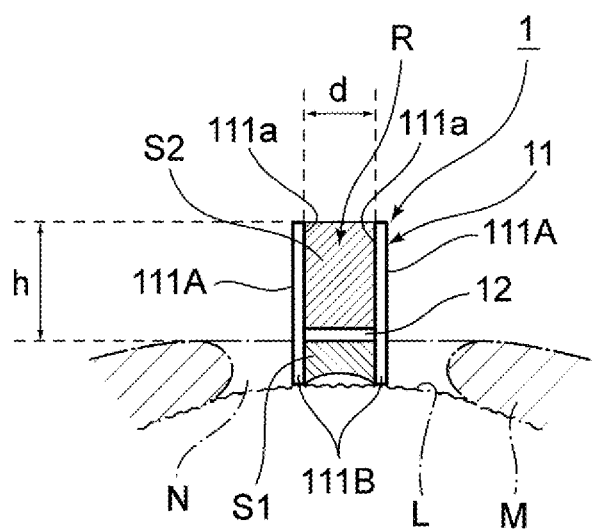
FIG. 4 is a front view illustrating the set status of the draining device according to the first embodiment of the present disclosure.

Further, the connecting portion 12 connects the lower center portions of the adjacent side wall members 111 and 111 as mentioned above, and therefore when the draining device 1 is placed or arranged on an eyelid M or the vicinity thereof, as shown in FIGS. 3 and 4, the lower surface 12a of the connecting portion 12 comes into contact with the eyelid M or the vicinity thereof. This enables stable arrangement of the draining device 1. Further, in this embodiment, the lower surface 12a of the connecting portion 12 is provided with an adhesive material. With this adhesive material, the connecting portion 12 can be adhered to the eyelid M or the vicinity thereof, which enables more stable arrangement/placement/mounting of the draining device 1.

[Setting Method of Draining Device 1]

Next, a method of setting (placing, arranging, or putting) the draining device 1 will be explained with reference to FIGS. 2 to 4. In the following explanation, as shown in FIG. 2, an eyelid retractor Z1 for opening upper and lower eyelid margins N is set or placed at the eyelids M of a patient.

Further, in a normal eye surgery, although a drape is adhered on an eyelid M, such a drape is not illustrated for the convenience of explanation.

Figure 2:
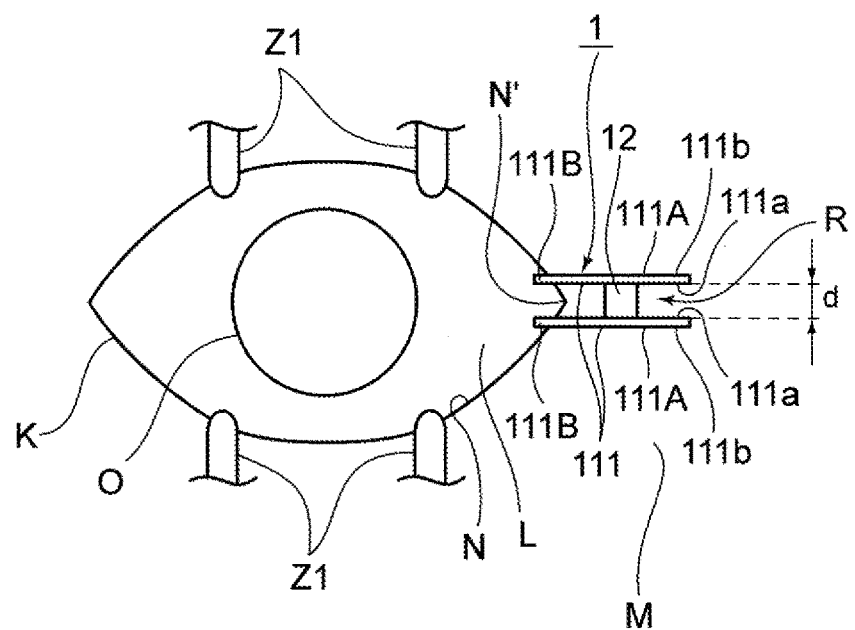
FIG. 2 is a plan view illustrating a set status of the draining device according to the first embodiment of the present disclosure.

In setting of the draining device 1, as shown in FIGS. 2 to 4, the draining device 1 is set so that the side wall members 111 and 111 of the main body 11 bridge the eyelid margins N. Concretely, the draining device 1 is placed so that the base sections 111A and 111A of the draining device 1 are placed or arranged on eyelids M and therearound near the canthus N' and each of the tip sections 111B is arranged so as to face the conjunctiva L in the eyelid aperture K.

In this state, as shown in FIG. 4, the tip sections 111B and 111B of the side wall members 111 and 111 are arranged at a predetermined distance d in an upright state with respect to the conjunctiva L. This increases an inflow cross-sectional area S1 for the liquid that flows in between the tip end sections 111B and 111B of the side wall members 111 and 111.

Further, as shown in FIG. 4, since the base sections 111A and 111A of the side wall members 111 and 111 are arranged side by side at a predetermined distance d therebeween in an upright state with respect to the eyelid M. This increases a passage cross-sectional area S2 for the liquid that flows in between the base sections 111A and 111A of the side wall members 111 and 111.

[Liquid Draining Mechanism of Draining Device 1]

Next, the liquid draining mechanism of the draining device 1 will be explained with reference to FIGS. 2 to 4.

At the time of eye surgery, as shown in FIGS. 2 to 4, the draining device 1 is set or placed as mentioned above, and in this state a liquid is supplied in the eyelid aperture K from a syringe, a surgical instrument, etc.

Then, as shown in FIG. 4, the liquid accumulated or stagnated in the eyelid aperture K flows in between the tip sections 111B and 111B by being sucked by the tip sections 111B and 111B due to the capillary action or the Coanda effect of the gap between the tip sections 111B and 111B of the side wall members 111 and 111.

At this time, the inflow cross-sectional area S1 at the position where a liquid flows in (the position shown by the broken line A in FIG. 3) is defined by the region surrounded by the conjunctiva L and the tip sections 111B and 111B. The tip sections 111B and 111B are arranged in parallel or side by side at a predetermined distance d in an upright state with respect to the conjunctiva L, causing a capillary action or a Coanda effect in approximately the entire region. This enables absorption of the liquid stagnated or accumulated in the eyelid aperture K from the tip end sections 111B and 111B and flow of the liquid therebetween in a manner such that approximately the entire region is filled with the liquid.

Figure 15A:
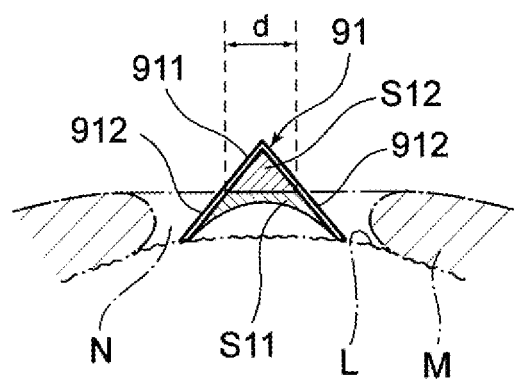
FIG. 15(a) is a front view illustrating a set status of a first conventional draining device.
Figure 15B:
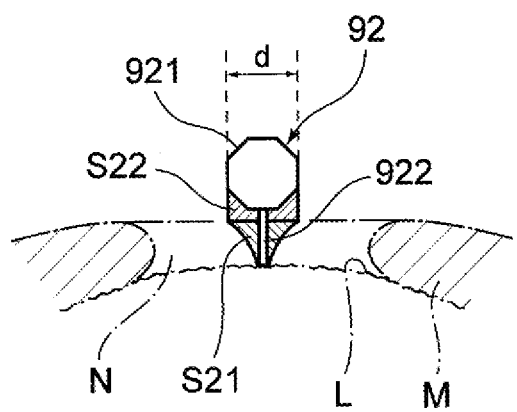
FIG. 15(b) is a front view illustrating a set status of a second conventional draining device.

In this regard, when comparing the draining device 1 of this embodiment with conventional draining devices 91 and 92 shown in FIGS. 15(a) and 15(b) having the same size as in this embodiment, as shown in FIGS. 4 and 15, the inflow cross-sectional area S1 of the draining device 1 of this embodiment is defined by approximately the entire region surrounded by the conjunctiva L and the tip sections 111B and 111B, whereas the inflow cross-sectional area S11 and S21 of each of conventional draining devices is very small. This is because of the following reasons. In the case of the conventional draining device 91, since the lower sides of the protruded portions 912 and 912 are excessively separated, the capillary action or the Coanda effect hardly occurs, which enables absorption of only the liquid near the lower surface of the main body 911 (see FIG. 15(a)). Further, in the case of the draining device 92, since it is formed by a single hook portion 922, the capillary action or the Coanda effect occurs only at the vicinity of the hook portion 922 (see FIG. 15(b)). In either case, the capillary action or the Coanda effect causing inflow of a liquid is not fully exerted. In the present draining device 1, the inflow cross-sectional area S1 of the liquid in the liquid draining passage R is large, which makes it possible for the draining device 1 to inflow a large amount of liquid from between the tip sections 111B and 111B.

The liquid flowed into the gap between the tip sections 111B and 111B of both the side wall members 111 and 111 passes through the gap between the base sections 111A and 111A of the side wall members 111 and 111 rearward by the capillary action, the Coanda effect or the like.

At this time, as shown in FIG. 4, the passage cross-sectional area S2 at the position (position shown by the broken line B in FIG. 3) where the liquid passes is a cross-sectional area of the region surrounded by the eyelid M and the base sections 111A and 111A. At this time, the base sections 111A and 111A are arranged in parallel at a predetermined distance d in an upright state with respect to the eyelid M, causing a capillary action or a Coanda effect in approximately the entire region. This enables the liquid to pass through the gap between the base sections 111A and 111A in a state in which approximately the entire region is filled with the liquid.

In this regard, for example, when comparing the conventional draining device 91 and 92 shown in FIGS. 15(a) and 15(b) having the same size as in the draining device 1 of this embodiment, as shown in FIGS. 4, 15(a), and 15(b), the passage cross-sectional area S2 of the draining device 1 of this embodiment is a cross-sectional area of a rectangular shape of a portion having a width d surrounded by the eyelid M and the base sections 111A and 111A. On the other hand, the passage cross-sectional area S12 and S22 of the conventional draining device 91 and 92 is a cross-sectional area of a portion of an approximately triangular shape having a base of a lateral width d (see FIG. 15(a)) or a cross-sectional area of the lower small gap portion of the draining device 92 (see FIG. 15(b)). The passage area S21 and S22 of the conventional draining device 91 and 92 is very small. In the present draining device 1 of this embodiment, since the liquid passage cross-sectional area S2 of the liquid draining passage R is large, the draining device 1 enables passing of a large amount of liquid through the gap between the base sections 111A and 111A.

As explained above, the liquid draining passage R for draining a liquid to the gap formed between the adjacent side wall members 111 and 111 is formed, and therefore the liquid inflow cross-sectional area S1 of the liquid draining passage R can be increased. As a result, it becomes possible to make a large amount of liquid flow into the gap between the side wall members 111 and 111. Further, since the liquid passage cross-sectional area S2 of the liquid draining passage R increases, a large amount of liquid can be flowed into the gap between the side wall members 111 and 111. As explained above, both the inflow cross-sectional area Si and the passage cross-sectional area S2 of the liquid draining passage R can be increased, enabling a large amount of the liquid to flow in and pass through the liquid draining passage R. This makes it possible to effectively drain the liquid stagnated or accumulated in the eyelid aperture K outside the eyelid aperture K.

Further, in view of the above, the space occupied by the present draining device 1 can be reduced by constituting the present draining device 1 so as to have a liquid draining efficiency (inflow cross-sectional area S1 and the passage cross-sectional area S2) equal to or similar to the liquid draining efficiency of the conventional draining devices 91 and 92 by, e.g., decreasing the height h of each side wall member 111 and/or decreasing the distance d between the side wall members 111 and 111. For this reason, it becomes possible for an operator performing surgery while sitting on the patient's ear side to more easily manipulate surgical instruments or tools.

Figure 5A:
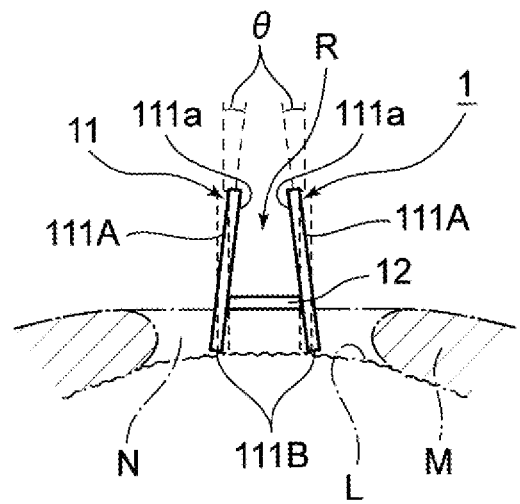
FIG. 5(a) is a front view illustrating a set status of a first modification of the draining device shown in FIG. 1.
Figure 5B:
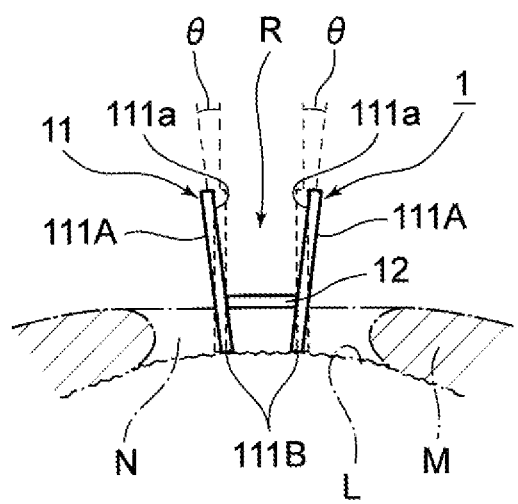
FIG. 5(b) is a front view illustrating a set status of a second modification of the draining device shown in FIG. 1.

In the aforementioned embodiment, the explanation was directed to the case in which the adjacent side wall members 111 and 111 are arranged so that the inner side surfaces 111a and 111a thereof face each other in parallel. However, the present invention does not always require that the inner side surfaces are arranged in parallel. For example, the side wall members 111 and 111 can be arranged so as to face each other in a manner such that the side wall members 111 and 111 are inclined so as to increase the distance therebetween toward the lower side (see FIG. 5(a)). Alternatively, for example, the side wall members 111 and 111 can be arranged so as to face each other in a manner such that the side wall members 111 and 111 are inclined so as to decrease the distance therebetween toward the lower side (see FIG. 5(b)). In summary, it should be noted that the present invention allows any modifications as long as the side wall members 111 and 111 are arranged in a manner such that at least the upper end portions of the side wall members 111 and 111 are arranged at a predetermined distance and that the inner side surfaces 111a and 111a of the adjacent side wall members 111 and 111 face each other. However, in order to enhance the liquid draining effect by increasing the distance between the side wall members 111 and 111, it is preferable to set the inclination angle of each side wall member 111 within a range of −20 degree to +20 degree with respect to the vertical direction (i.e., direction perpendicular to the placement surface such as an eyelid, etc.).

Further, the above explanation was directed to the case in which a hairline process is performed on the inner side surfaces 111a and 111a of the side wall members 111 and 111. However, in the present invention, a honing process for forming minute/fine irregular (concave-convex) shapes on the inner side surfaces 111a and 111a of the side wall members 111 and 111 can be performed in place of the hairline process, or both the hairline process and the honing process can be performed.

Further, the above explanation was directed to the case in which the side wall member 111 is made of a hard material. However, the side wall member 111 can be made of a water absorbing material.

Further, the above explanation was directed to the case in which the present draining device 1 is placed or arranged on the eyelid M (canthus N'). However, the draining device 1 can be placed or arranged on any positions other than the canthus N'.

<Second Embodiment>

Next, a second embodiment of a draining device according to the present disclosure will be explained with reference to FIG. 6. In this embodiment, the explanation will be directed only to the structure different from the structure of the first embodiment, and the explanation of the same structure will be omitted by allotting the same symbol to the corresponding portion.

Figure 6:
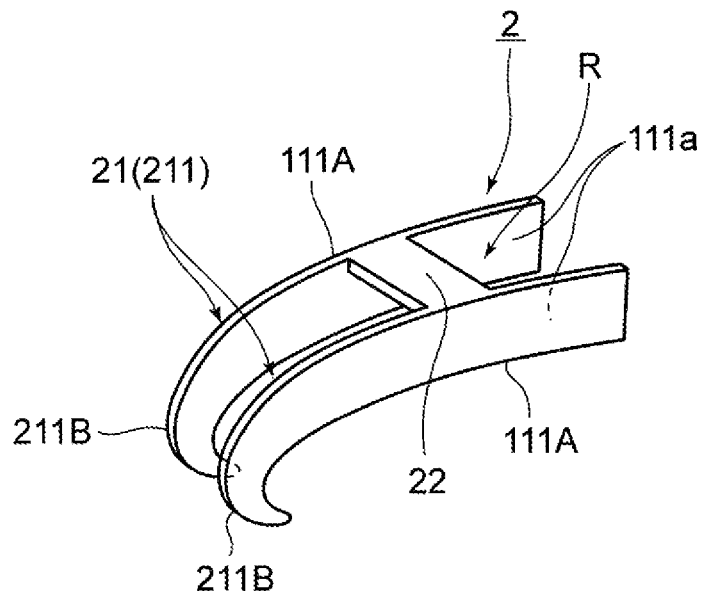
FIG. 6 is a perspective view illustrating a draining device according to a second embodiment of the present disclosure.

In the draining device 2 of this second embodiment, as shown in FIG. 6, the main body 21 is formed so that the tip section 211B of each of the side wall members 211 constituting the main body 21 is curved into a hook shape. Therefore, when the tip section 211B is hooked on the eyelid margin N, the draining device 2 can be placed or arranged stably.

Further, in this draining device 2, the connecting portion 22 is provided so as to connect the upper edges of the side wall members 211 and 211 constituting the main body 21, which makes it possible to smoothly pass a liquid in between the side wall members 211 and 211.

<Third Embodiment>

Next, a third embodiment of a draining device according to the present disclosure will be explained with reference to FIG. 7. In this embodiment, the explanation will be directed only to the structure different from the structure of the first embodiment, and the explanation of the same structure will be omitted by allotting the same symbol to the corresponding portion.

Figure 7:
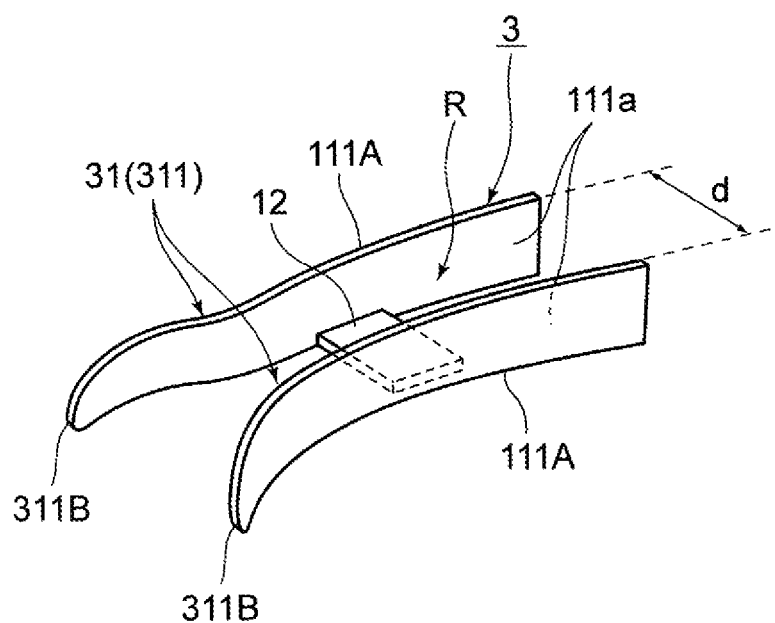
FIG. 7 is a perspective view illustrating a draining device according to a third embodiment of the present disclosure.

In the draining device 3 of this third embodiment, as shown in FIG. 7, the main body 31 is formed in a manner such that the tip sections 311B and 311B of the side wall members 311 and 311 are curved in a separating direction. This widens the inflow port for introducing a liquid to allow introduction of a more large amount of liquid.

<Fourth Embodiment>

Next, a fourth embodiment of a draining device according to the present disclosure will be explained with reference to FIG. 8. In this embodiment, the explanation will be directed only to the structure different from the structure of the first embodiment, and the explanation of the same structure will be omitted by allotting the same symbol to the corresponding portion.

Figure 8:
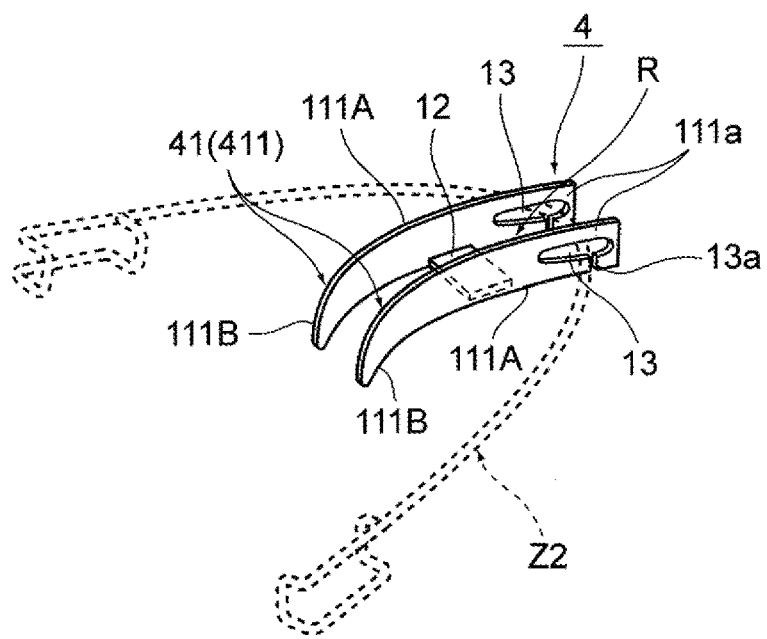
FIG. 8 is a perspective view illustrating a draining device according to a fourth embodiment of the present disclosure.

In the draining device 4 of this fourth embodiment, as shown in FIG. 8, each of the side wall members 411 and 411 constituting the main body 41 is provided, at its rear end section, with an insertion hole 13. A wire type eyelid retractor Z2 is attached to the draining device 4 in a manner such that the wire portion of the wire type eyelid retractor Z2 is inserted in the insertion holes 13 of the side wall members 411 and 411. According to this draining device 4, it becomes possible to drain a liquid in the eyelid aperture while opening the eyelid margins N using a general wire type eyelid retractor Z2.

Each side wall member 411 is provided with a cutout portion 13a formed below the insertion hole 13 so that the wire portion of the wire type eyelid retractor Z2 can be fitted in the insertion hole 13 via the cutout portion 13a.

<Fifth Embodiment>

Next, a fifth embodiment of a draining device according to the present disclosure will be explained with reference to FIG. 9. In this embodiment, the explanation will be directed only to the structure different from the structure of the first embodiment, and the explanation of the same structure will be omitted by allotting the same symbol to the corresponding portion.

Figure 9:
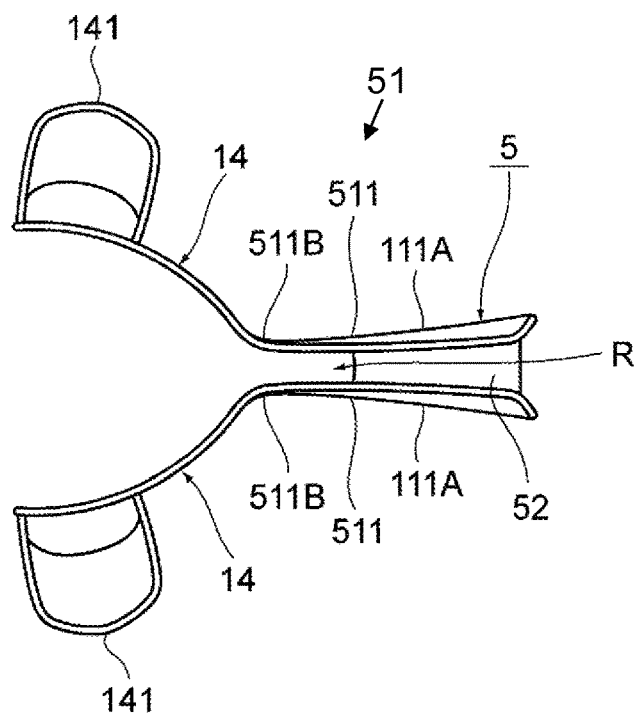
FIG. 9 is a plan view illustrating a draining device according to a fifth embodiment of the present disclosure.

In the draining device 5 of this fifth embodiment, as shown in FIG. 9, the main body 51 is provided with eyelid opening arms 14 and 14 each extending from the tip end section 511B of the side wall member 511 along the corresponding eyelid margin N. Each of the eyelid opening arms 14 is provided, at the tip section thereof, with a contact piece 141 which comes into contact with the inner surface of the eyelid margin N when used. Therefore, it becomes possible to drain the liquid in the eyelid opening while opening the upper and lower eyelids M with the eyelid opening arms 14 each extending from the tip section 511B.

Further, the connecting portion 52 of this draining device 5 is formed by an elastic member and connects the widthwise upper edge portions of the side wall members 511 and 511, so that the tip sections 511B and 511B can be urged in the separating direction. Therefore, when the tip sections 511B and 511 B are fixed to the eyelid margins N with the urging force, the draining device 5 can be placed stably.

<Sixth Embodiment>

Next, a sixth embodiment of a draining device according to the present disclosure will be explained with reference to FIG. 10. In this embodiment, the explanation will be directed only to the structure different from the structure of the first embodiment, and the explanation of the same structure will be omitted by allotting the same symbol to the corresponding portion.

Figure 10:
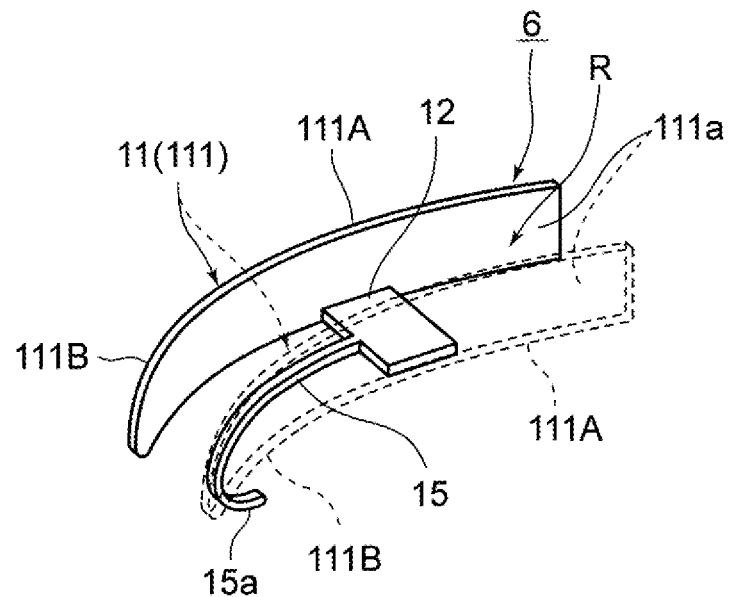
FIG. 10 is a perspective view illustrating a draining device according to a sixth embodiment of the present disclosure.

In the draining device 6 of this sixth embodiment, as shown in FIG. 10, the connecting portion 12 is provided with a fixing auxiliary member 15 extending from the connecting portion 12 along the length direction of the side wall member 111 between the side wall members 111 and 111 and having a hook-shaped tip section 15a. Therefore, when the tip section 15a of the fixing auxiliary member 15 is hooked on the eyelid margin N, the draining device 6 can be placed or arranged stably.

<Seventh Embodiment>

Next, a seventh embodiment of a draining device according to the present disclosure will be explained with reference to FIG. 11. In this embodiment, the explanation will be directed only to the structure different from the structure of the first embodiment, and the explanation of the same structure will be omitted by allotting the same symbol to the corresponding portion.

Figure 11:
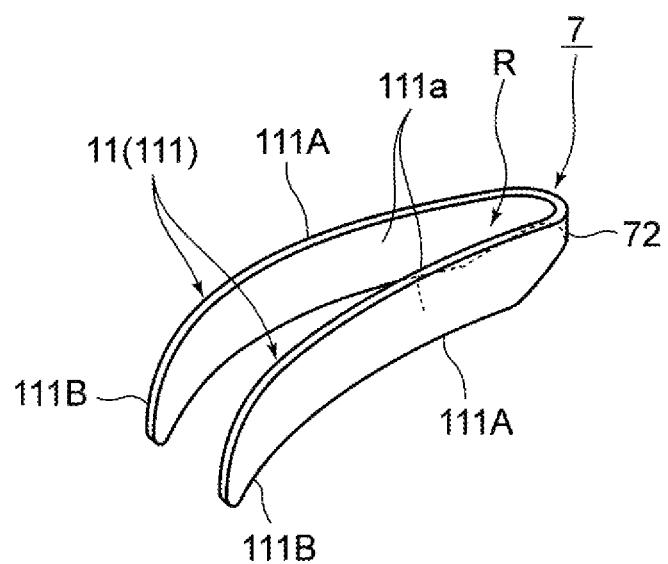
FIG. 11 is a perspective view illustrating a draining device according to a seventh embodiment of the present disclosure.

In the draining device 7 of this seventh embodiment, as shown in FIG. 11, the connecting portion 72 is a plate spring connecting rear end portions of the side wall members 111 and 111 in a manner such that the tip sections 111B and 111B of the side wall members 111 and 111 are urged in a separating direction. Therefore, when the tip sections 111B and 111B are fixed to the eyelid margins N with the urging force, the draining device 7 can be placed or arranged stably.

<Eighth Embodiment>

Next, an eighth embodiment of a draining device according to the present disclosure will be explained with reference to FIG. 12. In this embodiment, the explanation will be directed only to the structure different from the structure of the first embodiment, and the explanation of the same structure will be omitted by allotting the same symbol to the corresponding portion.

Figure 12:
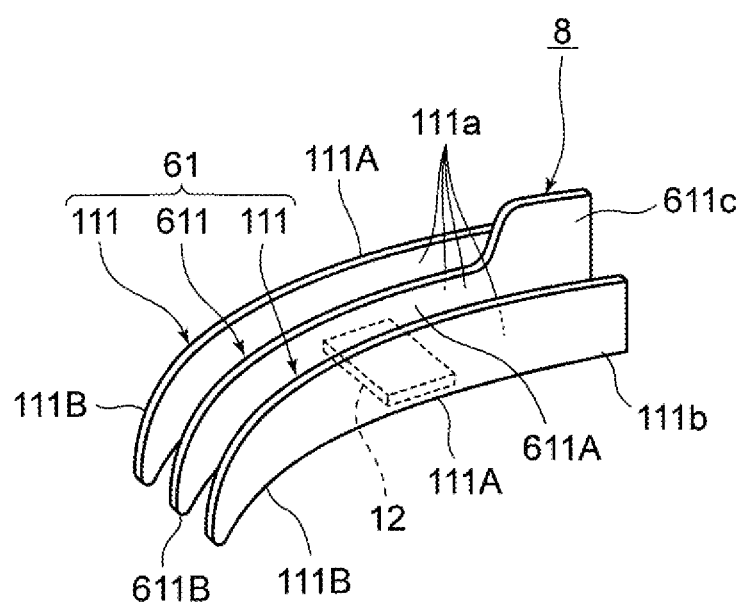
FIG. 12 is a perspective view illustrating a draining device according to an eighth embodiment of the present disclosure.

In the draining device 8 of this eighth embodiment, as shown in FIG. 12, one sheet of intermediate side wall member 611 is arranged between two sheets of side wall members 111 and 111. With this structure, the distance between adjacent side wall members 111 and 111 can be reduced, enhancing the capillary action or the Coanda effect and increasing the number of liquid draining passages, which enables assured draining of a large amount of liquid.

Further, the intermediate side wall member 611 is provided with a gripping part 611c at the rear upper portion of the base section 611A of the intermediate side wall member 611, and therefore the draining device 8 can be handled easily.

In this embodiment, the explanation was directed to the case in which the intermediate side wall member 611 is a single piece. However, the number of the intermediate side wall member 611 can be two or more.

<Ninth Embodiment>

Next, a ninth embodiment of a draining device according to the present disclosure will be explained with reference to FIGS. 13(a), 13(b), 13(c) and 14. In this embodiment, the explanation will be directed only to the structure different from the structure of the first embodiment, and the expla-nation of the same structure will be omitted by allotting the same symbol to the corresponding portion.

In the draining device 9 of this ninth embodiment, as shown in FIG. 13, the main body 71 is formed in a manner such that the tip sections 711B and 711B of the side wall members 711 and 711 are each curved into a hook-like shape and extended in the direction that the base section 711A extends. At the basal end of the tip section 711B, a protruded portion 711E protruding toward the tip end of the tip section 711B is provided. Further, the tip end of the tip section 711B is bent at a right angle in the inner direction of the main body 71 to form a bar 711D connecting the tips of the tip sections 711B and 711B. A gripping ledge 73 of an elongated plate-shaped member is extended from the bar 711D in the longitudinal direction of the main body 71.

Figure 13A:
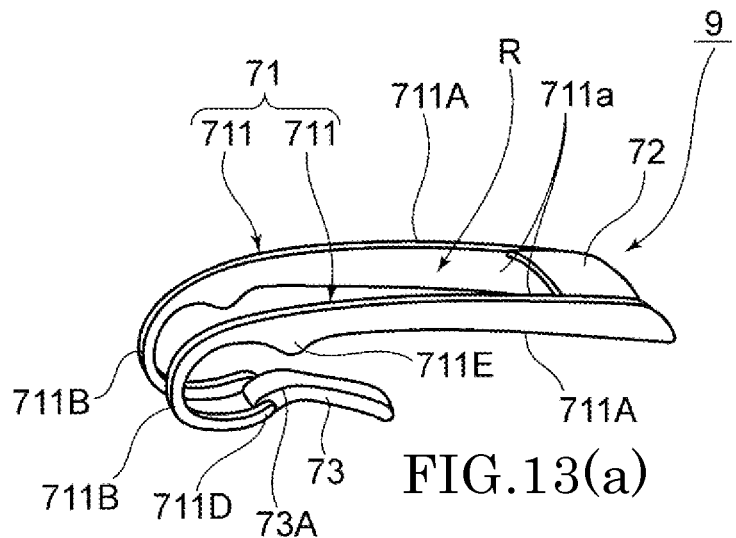
FIG. 13(a) is a perspective view of the draining device.
Figure 13B:
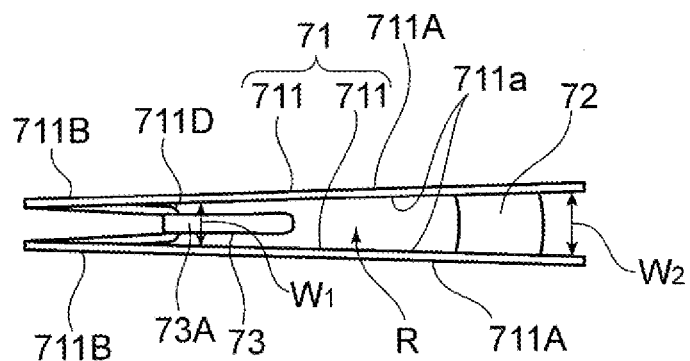
FIG. 13(b) is a plan view thereof.
Figure 13C:
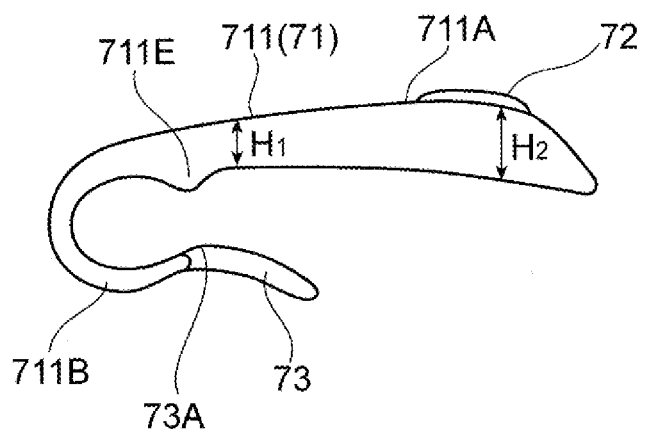
FIG. 13(c) is a side view thereof

The gripping ledge 73, as shown in FIG. 13(c), extends upward in the thickness direction while gently curving at the vicinity of the basal end (the portion connected to the bar 711D) and then extends downward in the thickness direction while gently curving as it departs from the vicinity of the basal end. The gripping ledge 73 of the aforementioned structure is provided with a protruded portion 73A at the vicinity of the basal end. The protruded portion 73A faces the protruded portion 711E of the main body 71. Further, the distance between the protruded portion 711E of the main body 71 and the protruded portion 73A of the gripping ledge 73 is set to be slightly smaller than a thickness of an eyelid margin N.

Figure 14:
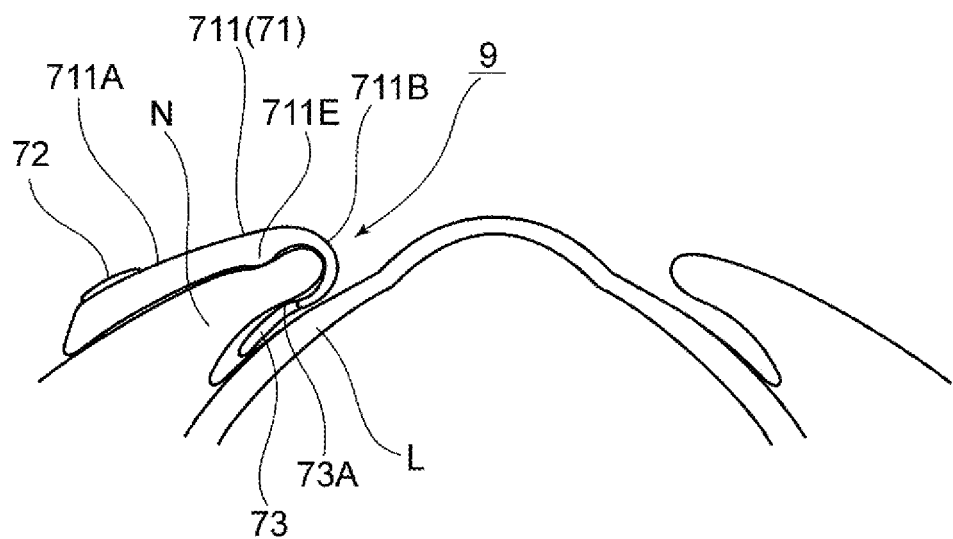
FIG. 14 is a side view illustrating a set status of the draining device of FIG. 13.

Thus, in the main body 71, when gripping the eyelid margin N, the tip section 711B elastically deforms so as to open in the thickness direction of the eyelid margin N. As a result, as shown in FIG. 14, the distance between the protruded portion 711E of the main body 71 and the protruded portion 73A of the gripping ledge 73 increases in accordance with the thickness of the eyelid and grips the eyelid margin N. Thus, the draining device 9 can be immediately and stably fixed. At the same time, the liquid draining ability can be increased.

As the material of the main body 71, for example, Nylon 12 (registered trademark) having biocompatibility and/or hydrophilicity, polyethylene, silicone, titanium, nonwoven fabric subjected to hydrophilic processing, can be preferably used. In this case, since the hydrophilicity of the material is high, the draining rate of a liquid can be improved.

Further, on the inner side 711a of the side wall member 711, a fiber having an irregular (concave-convex) surface, such as, e.g., a nonwoven fabric, can be adhered. In this case, since the liquid sucking function of the draining device 9 is improved, which results in an improved liquid draining rate.

Further, the side wall member 711 extends from the tip section 711B to the bar 711D, the liquid existing at the bottom portion of the eyelid of the outer lateral canthus or between the eyelid rear surface and the conjunctiva can be assuredly sucked up. Therefore, the liquid draining ability can be improved.

Further, the base section 711A of the side wall member 711 is preferably formed to be long. This increases the capacity for holding the liquid by the capillary action, resulting in an improved liquid sucking function of the draining device 9. Therefore, the liquid draining rate increases.

In FIGS. 13(b) and 13(c), by decreasing the width W1 of the tip sections 711B and 711B than the width W2 of the basal ends of the base sections 711A and 711A of the main body 71 or lowering the height H1 of the tip section than the height H2 of the basal end of the base section 711A, in accordance with the Bernoulli's principle related to liquid, the liquid draining rate can be increased.

In the embodiment shown in FIG. 13, only one gripping ledge 73 is provided. However, for example, a plurality of gripping ledges can be separately extended from the tip sections 711B.

Some embodiments of the present disclosure were explained with reference to the attached drawings. It should be noted, however, that the present disclosure is not limited to the illustrated embodiments. To the illustrated embodiments, various corrections and/or modifications can be added within the same scope of the present disclosure or the equivalent range thereof.

The terms and descriptions used herein are used only for explanatory purposes and the present invention is not limited to them. Accordingly, the present invention allows various design-changes falling within the claimed scope of the present invention.

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, the terminology "present invention" or "invention" is meant as a non-specific, general reference and may be used as a reference to one or more aspects within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features.

The invention claimed is:

1. A draining device for draining a liquid accumulated in an eyelid aperture to an outside of the eyelid aperture during eye surgery, comprising:
    a main body including a plurality of side wall members, wherein each of the plurality of side wall members includes an elongated plate-shaped member and each of the plurality of side wall members includes a tapered tip section curved downward; and
    a connecting portion connecting the side wall members of the main body,
    wherein, in a manner such that at least upper portions of adjacent side wall members are spaced at a certain distance and side surfaces of the adjacent side members are arranged in an upright state to face each other, by connecting the side wall members of the main body with the connecting portion,
    a liquid draining passage having a rectangular shape for draining a liquid in between adjacent side wall members is formed, wherein the liquid flows between the tapered tip sections into the liquid draining passage, the connecting portion arranged in the liquid draining passage.

2. The draining device as recited in claim 1, wherein the main body is formed so that a tip section of each of the plurality of side wall members is curved into a hook shape.

3. The draining device as recited in claim 1, wherein an inner side surface of each side wall member of the main body is subjected to a honing process or a hairline process.

4. The draining device as recited in claim 1, wherein the main body is made of a water absorbing material.

5. The draining device as recited in claim 1, wherein the main body is provided with an insertion hole at a rear end section of each of the plurality of side wall members, and a wire type eyelid retractor is attached to the draining device with a wire portion of the eyelid retractor inserted in the insertion hole.

6. The draining device as recited in claim 1, wherein the connecting portion is provided at lower end portions of the side wall members and includes an adhesive material on a lower surface of the connecting portion.

7. The draining device as recited in claim 1, wherein the connecting portion connects rear end portions of the side wall members in a manner as to urge the tip sections of the side wall members in a separating direction.

8. The draining device as recited in claim 1, wherein the connecting portion is provided with a fixing auxiliary member extending in a length direction of the side wall member between the side wall members and having a hook-shaped tip section.

9. A draining device for draining a liquid accumulated in an eyelid aperture, comprising:
    a plurality of side wall members each having a tapered tip section curved downward, wherein each of the plurality of side wall members includes an elongated plate-shaped member; and
    a connecting portion connecting the side wall members in a side-by-side manner, wherein the plurality of side wall members is arranged in an upright state so as to face each other with upper portions of the side wall members spaced at a certain distance,
    wherein the liquid flows from an inflow cross-sectional area between the tapered tip sections into a passage having a rectangular cross-sectional area between base sections of the plurality of side wall members, the connecting portion arranged in the passage cross-sectional area.

10. The draining device as recited in claim 9, wherein the plurality of side wall members are arranged substantially in parallel with each other.

11. The draining device as recited in claim 9, wherein a tip section of each of the plurality of side wall members is curved into a hook shape.

12. The draining device as recited in claim 9, wherein the inner side surface of the side wall member of the main body is subjected to a honing process or a hairline process.

13. The draining device as recited in claim 9, wherein each of the plurality of side wall members is made of a water absorbing material.

14. A method of draining a liquid in an eyelid aperture, comprising:
- preparing the draining device as recited in claim 9; and
- placing the draining device on an eyelid margin or vicinity thereof with the tip sections of the side wall members arranged in an eyelid aperture.

* * * * *